(12) United States Patent
Fabian et al.

(10) Patent No.: US 10,543,345 B2
(45) Date of Patent: Jan. 28, 2020

(54) FLUID DELIVERY DEVICE WITH POSITIONABLE TUBE

(71) Applicant: EasyNotes Ltd., Kfar Truman (IL)

(72) Inventors: Izhak Fabian, Kfar Truman (IL); Ilan Carmel, Tel Mond (IL); Omer Eilon, Tzur Itzhak (IL)

(73) Assignee: Easynotes Ltd., Kfar Truman (IL)

( * ) Notice: Subject to any disclaimer, the term of this patent is extended or adjusted under 35 U.S.C. 154(b) by 0 days.

(21) Appl. No.: 15/804,029

(22) Filed: Nov. 6, 2017

(65) Prior Publication Data

US 2019/0134361 A1    May 9, 2019

(51) Int. Cl.
| | | |
|---|---|---|
| *A61M 25/10* | (2013.01) | |
| *A61F 5/00* | (2006.01) | |
| *A61K 9/00* | (2006.01) | |
| *F16K 11/065* | (2006.01) | |
| *F16K 11/07* | (2006.01) | |
| *F16K 31/06* | (2006.01) | |

(52) U.S. Cl.
CPC ..... *A61M 25/10181* (2013.11); *A61F 5/0033* (2013.01); *A61F 5/0079* (2013.01); *A61K 9/0065* (2013.01); *F16K 11/0655* (2013.01); *F16K 11/07* (2013.01); *F16K 31/0613* (2013.01); *F16K 31/0617* (2013.01); *Y10T 137/3724* (2015.04); *Y10T 137/3786* (2015.04); *Y10T 137/86574* (2015.04); *Y10T 137/86614* (2015.04)

(58) Field of Classification Search
CPC ............ A61F 5/0079; A61F 5/0033; Y10T 137/86574; Y10T 137/86582; Y10T 137/86614; Y10T 137/3724; Y10T 137/3786; A61M 25/10181; A61K 9/0065; F16K 11/0655; F16K 11/07; F16K 31/0613; F16K 31/0617
See application file for complete search history.

(56) References Cited

U.S. PATENT DOCUMENTS

| | | | | |
|---|---|---|---|---|
| 4,524,951 A | * | 6/1985 | Green ................. | F16K 11/0655 137/625.25 |
| 4,598,699 A | * | 7/1986 | Garren ................. | A61B 1/2736 604/909 |
| 6,209,970 B1 | * | 4/2001 | Kamiya ................. | B60T 8/363 137/596.17 |
| 6,289,921 B1 | * | 9/2001 | Neuhaus ............... | F15B 13/044 137/454.5 |
| 9,125,660 B2 | * | 9/2015 | Fabian ............. | A61B 17/12136 |
| 2008/0149874 A1 | * | 6/2008 | Fukano ...................... | F16K 7/16 251/264 |
| 2008/0319471 A1 | * | 12/2008 | Sosnowski ............ | A61F 5/0036 606/192 |

(Continued)

*Primary Examiner* — Atif H Chaudry
(74) *Attorney, Agent, or Firm* — Dekel Patent Ltd.; David Klein

(57) ABSTRACT

A fluid delivery device includes a tube coupled to an axial manipulator. The axial manipulator includes an elongate member arranged to move axially in a housing. The tube is in fluid communication with a fluid diverter which is arranged to move axially in the housing upon axial movement of the elongate member. Seals are provided to prevent fluid from leaking out of the housing. A fluid port is in fluid communication with the tube via the fluid diverter, such that fluid can flow in and out of the tube via the fluid port and the fluid diverter.

7 Claims, 3 Drawing Sheets

(56) References Cited

U.S. PATENT DOCUMENTS

| | | | |
|---|---|---|---|
| 2012/0303051 A1* | 11/2012 | Matsuura | A61B 1/00082 606/192 |
| 2014/0309682 A1* | 10/2014 | Fabian | A61B 17/12136 606/192 |
| 2015/0000774 A1* | 1/2015 | Sung | F16K 11/0708 137/624.27 |

* cited by examiner

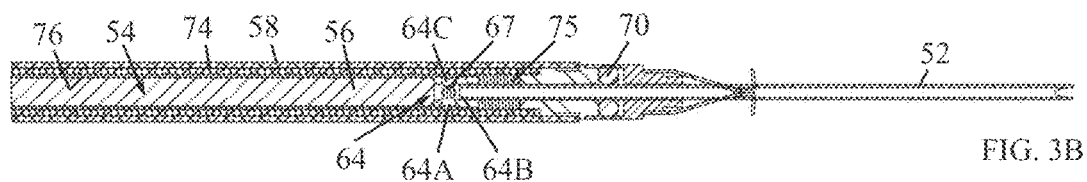
FIG. 3B
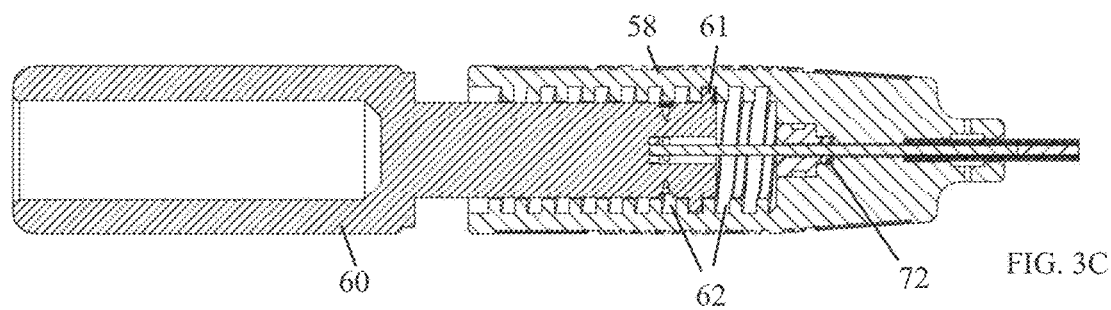
FIG. 3C
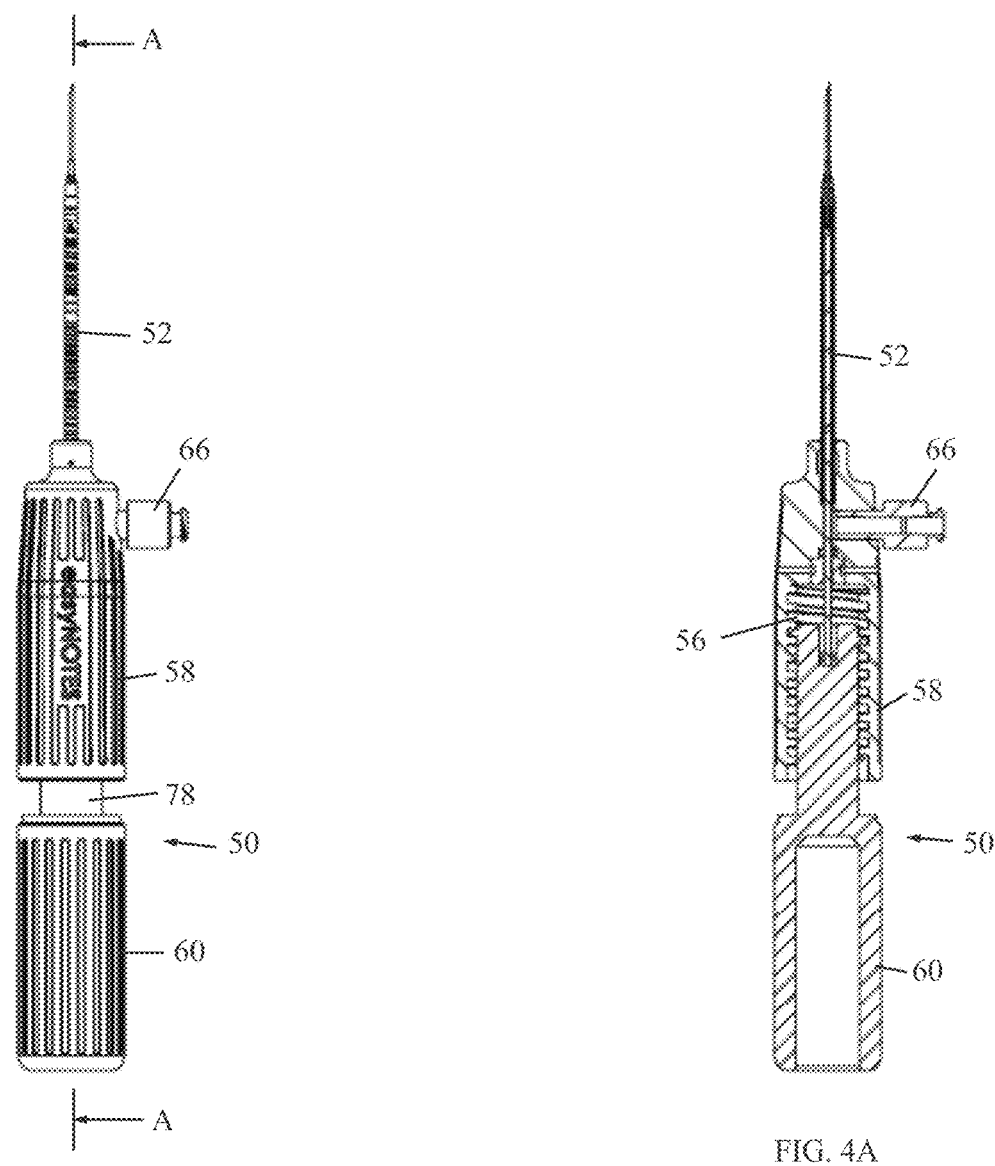
FIG. 4
FIG. 4A

FLUID DELIVERY DEVICE WITH POSITIONABLE TUBE

FIELD OF THE INVENTION

The present invention generally relates to fluid delivery devices, such as for introducing fluid for inflating balloons placed in body lumens and for extracting fluids from the balloons for their deflation, e.g., for inflating and deflating balloons used to obstruct or reduce flow of gastric contents across the pyloric valve.

BACKGROUND OF THE INVENTION

U.S. Pat. No. 9,125,660 describes an obstruction device (also called pyloric plug) for obstructing or reducing flow through a body lumen, in particular for obstructing or reducing flow of gastric contents across the pyloric valve (pylorus). The device is particularly useful in a transoral gastrointestinal procedure, but may be used in other laparoscopic, endoscopic, or natural orifice procedures in other body lumens. The plug is designed to be fully operative over a long time, and it can be removed and re-implanted.

The plug includes two balloons, one proximal and the other distal, mounted on a shaft. The proximal obstruction balloon is arranged to fit in the stomach, whereas the distal obstruction balloon is arranged to fit in the duodenum. When inflated, both balloons expand towards the pylorus from opposite sides on the pylorus, thus fixing the plug in place.

The plug is particularly useful to stop the flow of stomach contents to the proximal gut which includes the duodenum and the initial part of the jejunum. Such a need arises, for example, after creating an alternative path of flow through a gastro-jejunum anastomosis which bypasses the proximal gut. There could be other cases when this need arises, such as after surgery in the duodenum area or in the pancreas or bile outputs to the duodenum. Another indication could be the need to operate endoscopically on the stomach with an inflated stomach. In this case, the plug keeps the inflating air in the stomach and it does not bloat the intestine.

FIG. 1A illustrates the obstruction device 10 and delivery system 20 of U.S. Pat. No. 9,125,660. Obstruction device 10 includes a proximal obstruction balloon 12 and a distal obstruction balloon 14 mounted on a shaft 16. A portion of shaft 16, referred to as neck 18, provides a gap between proximal balloon 12 and distal balloon 14. Neck 18 can have different lengths and thicknesses depending on the application; for example, the dimensions of neck 18 are correlated to the usual width of the pylorus muscle.

The proximal obstruction balloon 12 is arranged to fit in the stomach, whereas the distal obstruction balloon 14 is arranged to fit in the duodenum. When inflated, balloons 12 and 14 expand towards the pylorus from opposite sides on the pylorus, thus fixing the plug 10 in place.

Distal obstruction balloon 14 may include a plurality of internal or external anchoring arms 19. One purpose of arms 19 is to help anchor the device against the pylorus in the duodenum. Another purpose is to create a non-uniform surface for pushing against tissue (e.g., the distal side of the pylorus). The non-uniform surface may help prevent creating constant pressure against the duodenal side of the pylorus; constant pressure has the disadvantageous risk of causing a sore, like a pressure sore, on the tissue Delivery system 20 includes an insertion tool 22 (separate from the plug) and an injection site assembly 24 assembled with one of the balloons, preferably, but not necessarily, the proximal balloon 12. Insertion tool 22 includes a shaft 26 that has a hollow lumen 27 for passing therethrough an inflation tube 28 (tube, catheter or syringe and the like). The distal end of shaft 26 is provided with a connector 30, which connects to injection site assembly 24 and which permits passing injection tools, injection fluid and other tools or substances therethrough.

Connector 30 may include a plurality of resilient fingers 32 (made of a suitable resilient, medically safe material, e.g., stainless steel, NITINOL or others) which serve as leaf springs. Injection site assembly 24 includes a proximal insertion port 34 and a distal receiving member 36, the proximal insertion port 34 being smaller in diameter than the distal receiving member 36. Injection site assembly 24 further includes a proximal septum 38, which serves as the proximal injection site 38, and a distal septum 40, which serves as the distal injection site 40, which is axially spaced from the proximal injection site 38. An inflation lumen 42 extends through shaft 16 and is in fluid communication with one or more proximal inflation ports 44 for inflation of proximal balloon 12 and with one or more distal inflation ports 46 for inflation of distal balloon 14.

In FIG. 1B, inflation tube 28 has advanced distally through both proximal injection site 38 and distal injection site 40. Distal balloon 14 is inflated with saline, air or other fluid, from a fluid source (not shown) flowing through distal inflation port 46. In FIG. 1C, inflation tube 28 is withdrawn proximally so that distal septum 40 is now sealed and proximal balloon 12 is inflated with fluid flowing through proximal inflation port 44. Optionally, proximal balloon 12 could be inflated first. Each balloon expands in a required direction so that as it expands, it increases pressure on the pylorus.

Both balloons may be deflated by connecting tube 28 to a source of negative pressure (vacuum) and sequentially introducing tube 28 to each injection site; instead of injecting fluid to the balloon, the balloon is emptied by suction of fluid from the balloon.

SUMMARY OF THE INVENTION

The present invention seeks to provide an improved fluid delivery device for inflating and deflating balloons placed in body lumens, as is described more in detail hereinbelow. The device is particularly useful for inflating and deflating balloons located at proximal and distal sides of the pylorus, but may be used for other balloons as well.

One of the advantages of the fluid delivery device of the invention over the prior art is that the fluid does not flow in a tube the entire length of the device. Instead, the fluid is introduced to or drawn from a tube which is located towards the distal end of the device. A proximal, rigid (e.g., solid) rod or other elongate member is used to advance or retract the tube axially to different axial positions (such as a distal port for inflating or deflating a distal balloon and a proximal port, which is spaced axially from the distal port, for inflating or deflating a proximal balloon). The use of the rigid elongate member ensures that the tube is moved precisely to the desired axial position in response to the user's manipulation as opposed to the prior art flexible tube which does not always transfer the user's manipulation into axial movement of the tube but instead may sometimes cause the tube to bend or deform rather than move axially.

For a solid elongate member, the fluid flows around the outside contour of the elongate member before entering or exiting the tube.

There is thus provided in accordance with an embodiment of the present invention a fluid delivery device including a tube coupled to an axial manipulator, the axial manipulator including an elongate member arranged to move axially in a housing and the tube being in fluid communication with a fluid diverter which is arranged to move axially in the housing upon axial movement of the elongate member, seals configured to prevent fluid from leaking out of the housing, and a fluid port in fluid communication with the tube via the fluid diverter, such that fluid can flow in and out of the tube via the fluid port and the fluid diverter.

In accordance with a non-limiting embodiment of the present invention the elongate member is not hollow.

In accordance with a non-limiting embodiment of the present invention the elongate member is coupled to a manipulation handle.

In accordance with a non-limiting embodiment of the present invention the manipulation handle is connected by a threaded connection to the housing, wherein rotation of the manipulation handle moves the elongate member axially with respect to the housing.

In accordance with a non-limiting embodiment of the present invention the fluid diverter is located between a distal end of the elongate member and a proximal end of the tube.

In accordance with a non-limiting embodiment of the present invention the fluid diverter includes a first passage in fluid communication with the fluid port, a second passage in fluid communication with a proximal end of the tube and a third passage in fluid communication with fluid located around an outer contour of the elongate member.

In accordance with a non-limiting embodiment of the present invention a portion of the elongate member is located inside a plurality of coils and some of the coils are coupled to the tube.

In accordance with a non-limiting embodiment of the present invention the manipulation handle includes markings to indicate axial positioning of the tube.

BRIEF DESCRIPTION OF THE DRAWINGS

The present invention will be understood and appreciated more fully from the following detailed description taken in conjunction with the drawings in which:

FIG. 3B is an enlarged view of the distal end of the device of FIG. 3A;

FIG. 3C is an enlarged view of the proximal end of the device of FIG. 3A;

FIG. 4 is another simplified illustration of the fully assembled fluid delivery device;

FIG. 4A is a simplified sectional illustration of the fluid delivery device, taken along lines A-A in FIG. 4.

DETAILED DESCRIPTION OF EMBODIMENTS

Figure 1A:
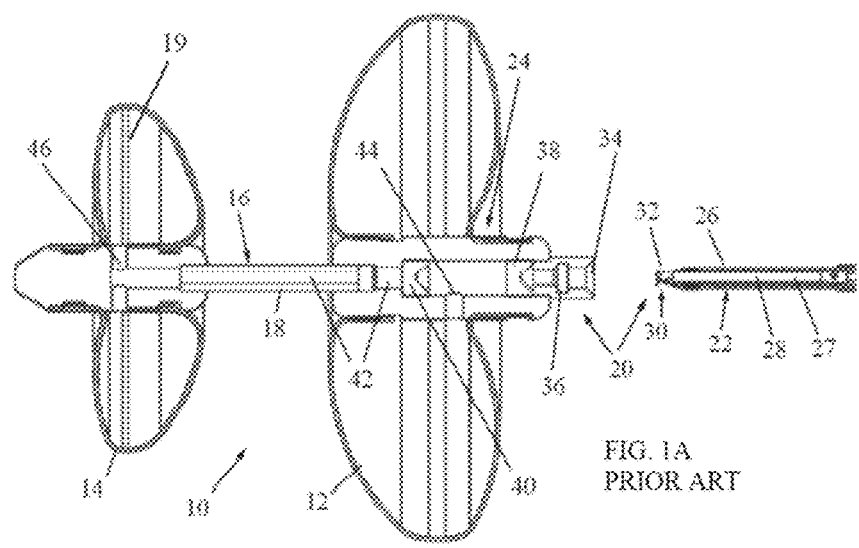
FIG. 1A is a simplified illustration of an obstruction device and delivery system of the prior art U.S. Pat. No. 9,125,660.
Figure 1B:
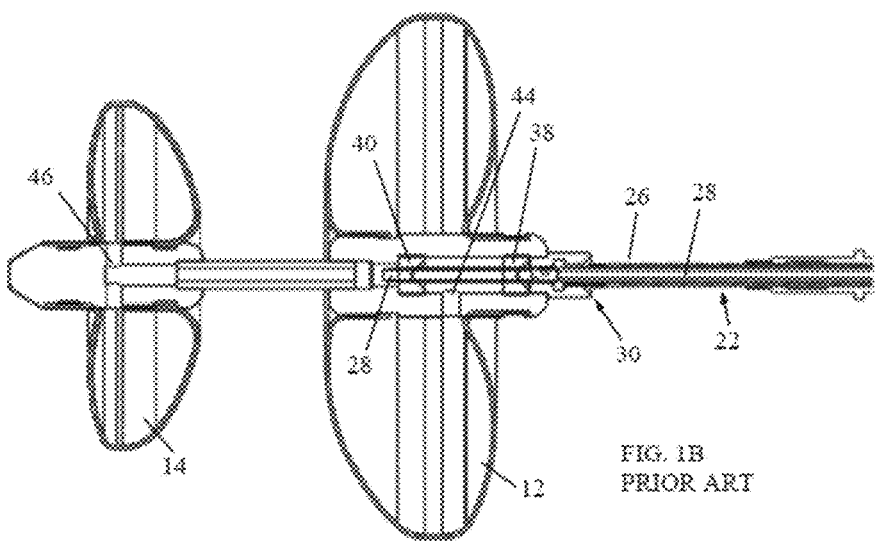
FIGS. 1B and 1C are simplified illustrations of using the delivery system to inflate distal and proximal balloons, respectively, of the obstruction device of the prior art U.S. Pat. No. 9,125,660.
Figure 1C:
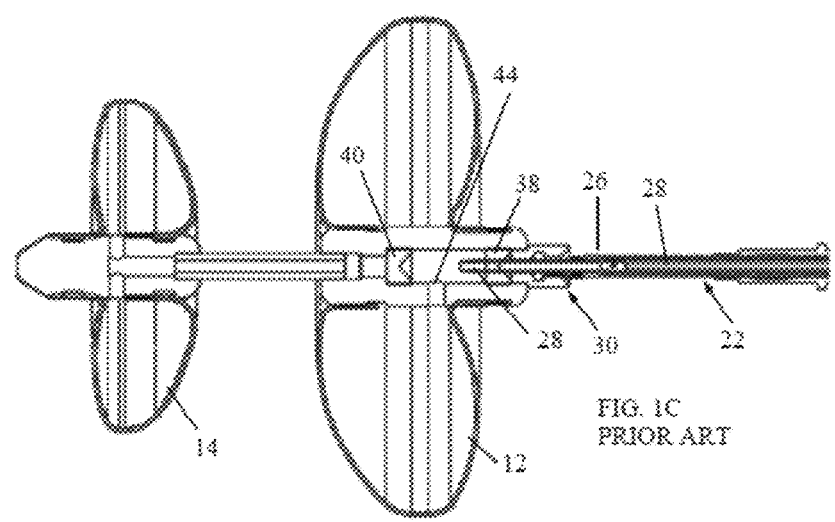
Figure 2:
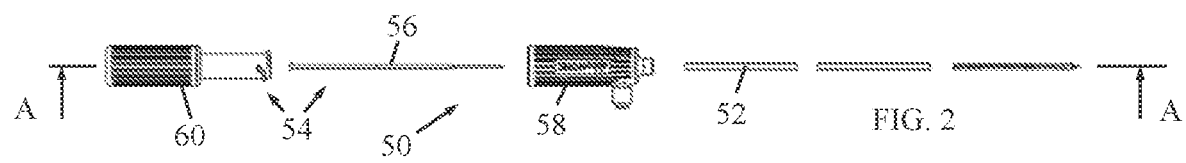
FIG. 2 is a simplified, exploded illustration of a fluid delivery device, constructed and operative in accordance with an embodiment of the present invention.
Figure 2A:
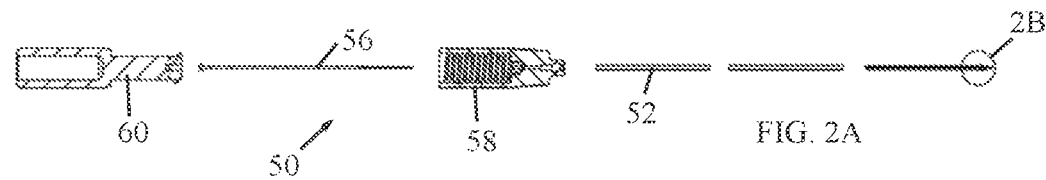
FIG. 2A is a simplified sectional illustration of the fluid delivery device, taken along lines A-A in FIG. 2.
Figure 3:
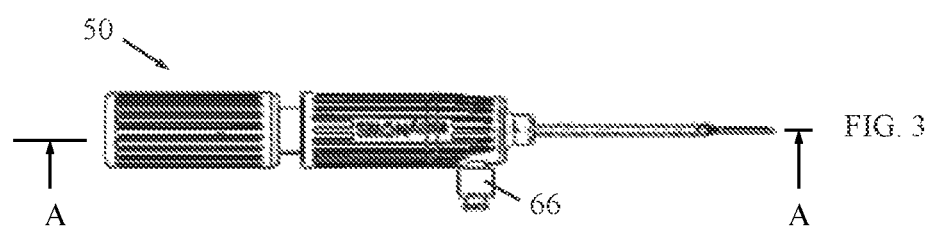
FIG. 3 is a simplified illustration of the fully assembled fluid delivery device.
Figure 3A:
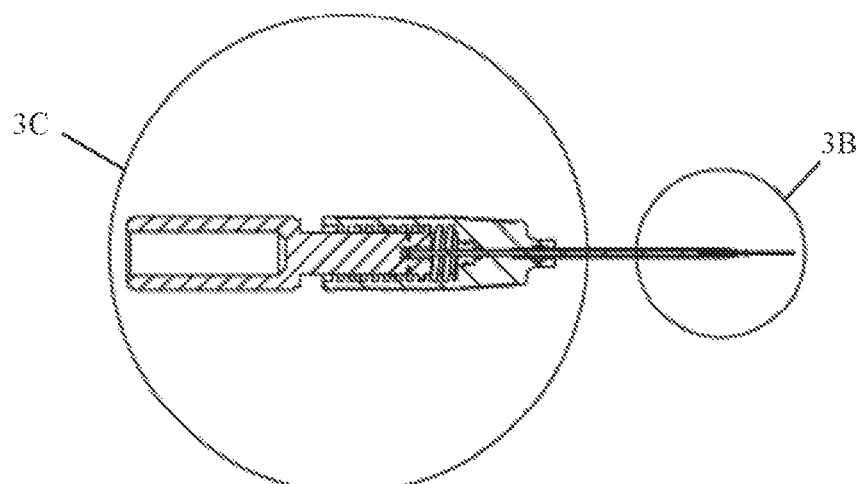
FIG. 3A is a simplified sectional illustration of the fluid delivery device, taken along lines A-A in FIG. 3.

Reference is now made to FIGS. 2-3C, which illustrate a fluid delivery device 50, constructed and operative in accordance with an embodiment of the present invention.

Fluid delivery device 50 includes a tube 52 coupled to an axial manipulator 54. The axial manipulator 54 includes an elongate member 56 arranged to move axially in a housing 58. The axial manipulator 54 may further include a manipulation handle 60 coupled to elongate member 56.

The manipulation handle 60 may be connected by a threaded connection to housing 58, such as by engagement of one or more male threads 61 with female threads 62 (FIG. 3C). Rotation of the manipulation handle 60 moves the elongate member 56 axially with respect to the housing 58.

In accordance with a non-limiting embodiment of the present invention the elongate member 54 is not hollow, such as but not limited to, a rigid solid rod or the like, e.g., made of stainless steel or other suitable material Tube 52 may be in fluid communication with a fluid diverter 64 (FIG. 3B) which is arranged to move axially in the housing 58 upon axial movement of the elongate member 54. Fluid diverter 64 may be located between a distal end of the elongate member 56 and a proximal end of the tube 52.

Fluid diverter 64 may include a first passage 64A in fluid communication with a fluid port 66 (such as a luer connector) affixed to housing 58. Fluid diverter 64 may include a second passage 64B in fluid communication with a proximal end of the tube 52 and a third passage 64C in fluid communication with fluid located around an outer contour of the elongate member 56. A spherical element 67 may be located in the center of fluid diverter 64 to help divert the fluid flow into tube 52.

Different seals may be provided to prevent fluid from leaking out of housing 58, such as seal 70 on tube 52 and seal 72 on elongate member 56. When introducing fluid towards tube 52, fluid enters fluid port 66 and flows via first passage 64A to fluid diverter 64. Most of the fluid is diverted directly via second passage 64B into the proximal end of tube 52. Some of the fluid flows via third passage 64C to the gap around the outer contour of the elongate member 56. However, this fluid is trapped between seals 70 and 72 and cannot leak out of housing 58, so that most of the trapped fluid eventually enters tube 52. The same holds true when drawing fluid from tube 52.

Accordingly, fluid port 66 is in fluid communication with tube 52 via fluid diverter 64, such that fluid can flow in and out of tube 52 via fluid port 66 and fluid diverter 64.

Figure 2B:
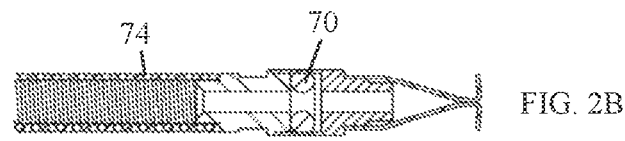
FIG. 2B is an enlarged view of the distal end of the device of FIG. 2A.

In accordance with a non-limiting embodiment of the present invention a portion of the elongate member 56 is located inside a plurality of coils 74 (FIGS. 2B and 3B). Some of the coils 74 may be coupled to tube 52 via a threaded insert 75 (FIG. 3B). As seen in FIG. 3B, a sleeve 76 may be placed between elongate member 56 and coils 74.

In accordance with a non-limiting embodiment of the present invention the manipulation handle 60 may include one or more markings 78 to indicate axial positioning of tube 52.

What is claimed is:

1. A fluid delivery device comprising:
a tube coupled to an axial manipulator, said axial manipulator comprising an elongate member arranged to move axially in a housing and said tube being in fluid communication with a fluid diverter which is arranged to move axially in said housing upon axial movement of said elongate member;

seals configured to prevent fluid from leaking out of said housing; and a fluid port in fluid communication with said tube via said fluid diverter, such that fluid can flow in and out of said tube via said fluid port and said fluid diverter, and wherein a proximal end of said tube is received in a cutout distal portion of said axial manipulator, and wherein said fluid diverter is located between a distal end of said elongate member and a proximal end of said tube.

2. The fluid delivery device according to claim 1, wherein said elongate member is not hollow.

3. The fluid delivery device according to claim 1, wherein said elongate member is coupled to a manipulation handle.

4. The fluid delivery device according to claim 3, wherein said manipulation handle is rotatable to move said elongate member axially with respect to said housing.

5. The fluid delivery device according to claim 3, wherein said manipulation handle comprises markings to indicate axial positioning of said tube.

6. The fluid delivery device according to claim 1, wherein said fluid diverter comprises a first passage in fluid communication with said fluid port, a second passage in fluid communication with a proximal end of said tube and a third passage in fluid communication with fluid located around an outer contour of said elongate member.

7. The fluid delivery device according to claim 1, wherein a portion of said elongate member is located inside a plurality of coils and some of said coils are coupled to said tube.

* * * * *